United States Patent [19]

Bauer

[11] Patent Number: 5,074,790

[45] Date of Patent: Dec. 24, 1991

[54] SCREW IMPLANT FOR A JAWBONE

[76] Inventor: Ernst Bauer, Eleonoring 14, 6040 Bad Neuheim, Fed. Rep. of Germany

[21] Appl. No.: 436,594

[22] Filed: Nov. 15, 1989

[30] Foreign Application Priority Data

Jun. 5, 1989 [DE] Fed. Rep. of Germany ....... 3918309

[51] Int. Cl.$^5$ .............................................. A61C 8/00
[52] U.S. Cl. ..................................................... 433/174
[58] Field of Search ................ 433/173, 174, 175, 176

[56] References Cited

U.S. PATENT DOCUMENTS

| 3,386,169 | 6/1968 | Scialom | 433/173 |
|---|---|---|---|
| 3,590,485 | 7/1971 | Chercheve et al. | 433/174 |
| 4,406,623 | 9/1983 | Grafelmann et al. | 433/174 |
| 4,424,037 | 1/1984 | Ogino et al. | 433/201.1 |
| 4,468,200 | 8/1984 | Muench | 433/174 |
| 4,645,453 | 2/1987 | Niznick | 433/173 |
| 4,758,160 | 7/1988 | Ismail | 433/174 |
| 4,758,161 | 7/1988 | Niznick | 433/173 |
| 4,767,328 | 8/1988 | Branemark | 433/173 |

FOREIGN PATENT DOCUMENTS

| 2255916 | 5/1974 | Fed. Rep. of Germany . |
|---|---|---|
| 2600639 | 7/1976 | Fed. Rep. of Germany . |
| 3136602 | 8/1982 | Fed. Rep. of Germany . |
| 3241963 | 4/1984 | Fed. Rep. of Germany . |
| 3421056 | 12/1985 | Fed. Rep. of Germany ...... 433/174 |
| 515709 | 1/1972 | Switzerland . |

OTHER PUBLICATIONS

Tetsch, Peter: Enossale Implantationen in der Zahnheilkunde, Munich/Vienna: Carl Hanser-Verlag (1984), pp. 117-120.

Primary Examiner—John J. Wilson
Assistant Examiner—Michael Lynch
Attorney, Agent, or Firm—Marshall, O'Toole, Gerstein, Murray & Bicknell

[57] ABSTRACT

A screw implant for a jawbone has a conical threaded implant body with an implant neck and a conical implant post to accept a replacement tooth or a substructure. The thread of the implant body is a compression thread with concave thread turns.

The implant neck preferably defines a bending zone wherein the ratio of the diameter $D_B$ to the length $L_B$ of the bending zone is in the range of 1:1.5 to 1:3. The bending angle is up to 30 degrees and the number of bendings of the bending zone is 3 to 4, when the implant post is bent back and forth. The implant neck has broadening transition sections.

13 Claims, 3 Drawing Sheets

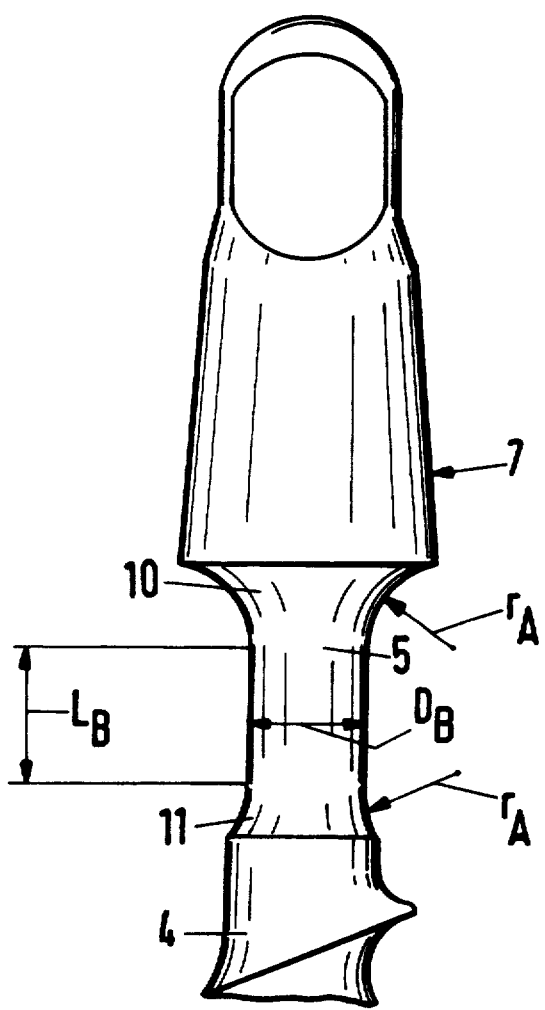

SCREW IMPLANT FOR A JAWBONE

BACKGROUND OF THE INVENTION

1. Field of the Invention

The invention relates to a screw implant for a jawbone comprising a threaded conical body which can be screwed into the jawbone, on which is formed an implant neck and a conical implant post to accept a replacement tooth or a substructure.

2. Description of Related Art

There are many forms of known tooth implants. Only a few of these have found practical application. For example, needle implants and blade or plate and screw implants have been used. Even though screw implants have been found to be especially useful, they have not fulfilled expectations. Proposed forms of such implants have been found to be deficient, especially because of insufficient anchoring, damage to the bone, or because of complicated insertion methods.

German Offenlegungschrift 22 55 916 (May 16, 1974) describes a screw implant which has a helical thread as well as a substantially constant outside diameter. Good initial anchoring is taught to be achievable and the anchoring effect is intended to improve as time progresses. However, it has been found that, since the diameter of the shaft is relatively large, the thread of the shaft cuts into the bone bed during implantation such that destruction of bone tissue cannot be avoided. Voids formed in the threads have an adverse influence on the lifetime of the implant, and also form infection sites. Furthermore, the rigid screw-in implant cannot be bent, as for straightening, after implantation. As a rule, it is only possible to shorten such an implant by grinding of the column or post carried by the implant neck. This is especially unpleasant for the patient, since the grinding has to be done after the insertion of the implant.

Another embodiment of a screw implant as described in Grafelmann, et al. U.S. Pat. No. 4,406,623 (Sept. 27, 1983) has a conical screw shaft with a helical thread. The purpose of this structure is to impart to the implant enhanced strength in the implanted state. It is clear from this patent that, in screw implants, the form of the thread is of special importance, and very precise data are given. V-shaped sections are cut out from the threads of the helical thread winding at angular distances which are smaller than 360° but not equal to 180°. These cuts are radially directed and, starting from the periphery of the helix, the tips are in the region of the shaft surface. Furthermore, sharpened parts which extend in the direction of insertion are formed. Thus, a very sharply cutting thread is provided and such an implant cuts into the bone relatively deeply. However, this results in bone tissue destruction and development of void spaces. Moreover, straightening of the implant is not possible and here, too, grinding processes must be employed for adaptation.

German Offenlegungschrift 26 00 639 (July 15, 1976) describes an insert for a tooth bed wherein the insert has a nonbendable strengthening extension and a thread, with the threads being cut deeply in such a way that, upon insertion, voids are formed between the insert and the tissues which may lead to inflammation.

A screw-type jaw implant made from ceramic materials is described in Munch U.S. Pat. No. 4,468,200 (Aug. 28, 1984). At a lower end, which is intended for anchoring in the jawbone, a conical screw having a rounded end is provided, and at its upper end is a hollow groove for attachment of the epithelial sleeve and has an opening to accept a tooth support. This is designed for insertion immediately after a tooth is extracted. There is an annular thickened portion between the upper and lower ends, which is designed as a conical screw and there are at least two annular notches, whereby the diameter of the annular thickened region is smaller than the diameter of the thread peaks at the uppermost thread of the lower part of the jaw implant. In order to achieve an especially secure anchoring, the lower part of the jaw implant is provided with sawtooth-like threads but a disadvantage of these is that the jaw tissue is damaged when the implant is inserted. The thread design does not permit elimination of voids. Moreover, the securing section for holding the replacement tooth cannot be adjusted.

It has long been known that an implant must be anchored permanently. In addition to eliminating or minimizing void spaces in the bone tissue, the implant should be supported at both ends in the bone, that is, it must be supported by the compact bone tissue of the alveolar countercorticalis. However, as a rule, the formation of voids can only be prevented when, during the insertion of the screw implant, there is no destruction of the bone tissue through which it travels. In the case of prior known screw implants, this cannot be prevented due to the relatively deep penetration of the cutting threads. However, as a result of the destruction of tissue and the development of voids around the implant, primary stability, on which later retention depends and which is responsible for a strong bond between the implant and bone, is not ensured. Especially in the front tooth region of the lower jaw, the length of the screw implant determines the degree of support by the bone tissue against which the implant lies during insertion. Therefore, either an implant with an accurate length must be used, or the end that protrudes from the jaw (i.e. the implant post) must be shortened or ground to the proper size.

SUMMARY OF THE INVENTION

It is an object of the invention to overcome one or more of the problems described above.

According to the invention, a screw implant is provided which can be inserted simply and without destruction or damage, without formation of weakening voids in the bone tissue and, as a result, which provides primary strength so that the implant can be used immediately after insertion. The screw implant can also be adapted by straightening of the implant post after the insertion of the implant.

Other objects and advantages will be apparent to those skilled in the art from a review of the following detailed description, taken in conjunction with the drawings and the appended claims.

DETAILED DESCRIPTION OF THE INVENTION

Figure 1:
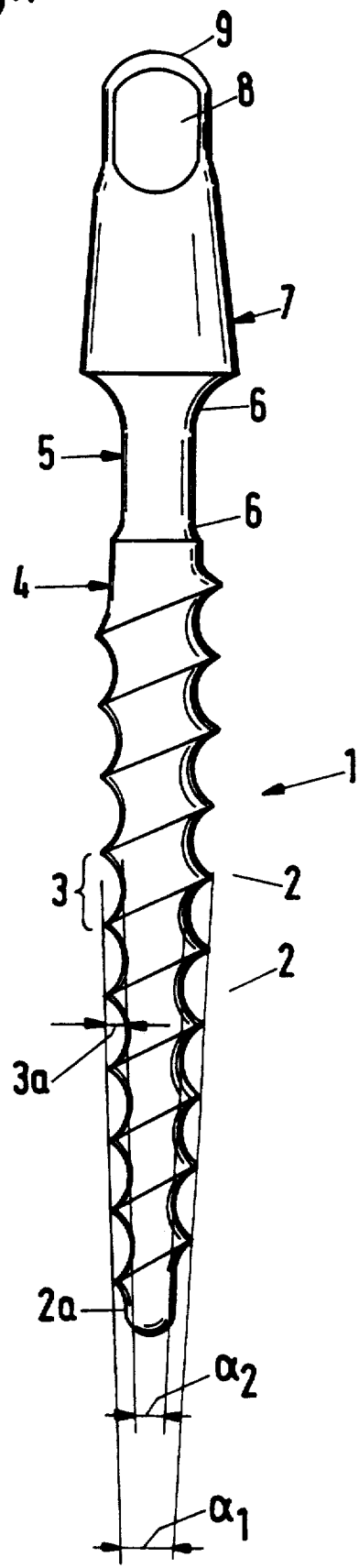
FIG. 1 is an elevation of a screw implant of the invention.

The screw implant of the invention has an implant body comprising compression threads having a concave design, as described in more detail below.

Referring to the drawings, the screw implant has a conical implant body, generally designated 1, with a compression thread 2 defined by concave thread turns 3. The implant body 1 is characterized by an outer boundary cone defining a cone angle $\alpha_1$. The thread core is also conical and defines an inner cone having a cone angle $\alpha_2$. A spherical tip 2a is defined at the lower end of the body 1.

The thread turns 3 are not necessarily circular, and have a maximum depth 3a which is preferably about one-third of the height of the thread turns 3.

Figure 2:
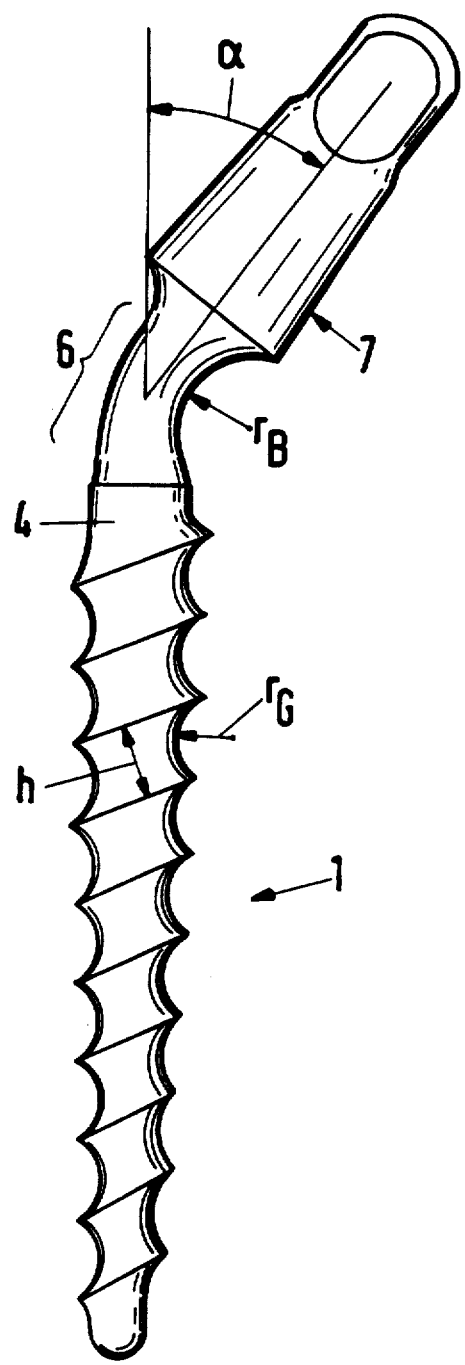
FIG. 2 is an elevation of the screw implant of FIG. 1 having a bent implant post; and, FIG. 3 is an enlarged elevation of the neck of the implant of FIGS. 1 and 2.

As shown in more detail in FIG. 2, the thread turns may be circular with a radius $r_G$ which is equal to about half of the thread pitch h. (In the drawings, the dimensions are not to scale.)

An implant shoulder 4 extends from the upper end of the compression thread 2. The shoulder 4 has an implant neck, generally designated 5, which defines a bending zone 6. The length of the bending zone 6 is designated $L_B$ and the diameter is designated $D_B$ (FIG. 3). An implant post 7 is defined at the upper end of the neck 5.

As shown in FIG. 3 on a larger scale, the implant neck 5 has two transition regions 10 and 11 which widen in the direction of the implant post 7 and the implant shoulder 4, respectively, and have a radius of curvature $r_A$, which can be the same magnitude for both transition regions 10 and 11. The implant post 7 narrows conically upward and, at an upper end region, defines two flat opposed areas 8. The flat areas 8 form a rectangle which serves for coupling an instrument, which is used as an aid for screwing in the implant, and for bending and straightening the post 7. A hemispherical head 9 is formed on the implant post 7. The cone of the implant post 7 (as seen from the tip edge) continues over the entire length of the post 7 without interruption, so that the guidelines are retained.

FIG. 2 shows the implant post 7 bent at an angle $\alpha_B$ to define a curve with a radius of curvature $r_B$ in the region of the bending zone 6. The radius $r_B$ is typically between 2 and 3 mm. Although a bending angle of up to 30 degrees is possible without damaging the implant neck, the bending zone 6 can be kept small if desired.

Since no alterations of the implant post 7 need be made before or after insertion thereof, standardized transfer caps with an inner cone complementary to the implant post 7 can be used. As a result, an exact impression can be made of the corresponding jaw region. Since the cone of the impression pin corresponds to that of the implant post 7, the impression gives the position of the implant precisely. Thus, the primary structure or substructures to be supported by the post will fit exactly.

The screw implant is preferably formed of a titanium alloy and its surface is preferably passivated with a protective layer of titanium oxide according to ASTM F 86-68.

After passage of the screw implant through the compact bone tissue of the alveolar chamber during insertion, the concave shaped compression thread of the screw implant subjects the spongy bone tissue to a gradually increasing pressure which results in extraordinarily high primary stability even during the screwing-in process. The bone tissue surrounding the implanted body is deformed within its elastic range, but is not destroyed.

The cone angle of the external boundary cone, $\alpha_1$, must be in a certain range of values. It has been found that deformation of the bone tissue remains within the range of elasticity of the bone tissue when the angle $\alpha_1$ is between 2 and 4 degrees, preferably between 2.7 and 3.5 degrees. Moreover, the design of the threads must be adapted to the angle $\alpha_1$ and to the elasticity of the bone tissue. It has been found that it is preferable when the ratio of the cone angle $\alpha_1$ of the external boundary cone to the cone angle $\alpha_2$ of the cone encompassing the thread core of the compression thread is in the range of 1:0.6 to 1:1. A preferred ratio is 1:0.85. The maximum outside diameter of the thread is 2 to 2.5 mm, which depends on the area of application (for example, molars).

When the concave design of the threads is substantially in the form of a circular arc, there is a gradual radial displacement of bone tissue which fills the rounded area between the helical threads, so that no voids occur and thus the adverse consequences thereof can be avoided. According to a preferred embodiment, the radius of curvature $r_G$ of each thread turn is greater than or equal to one-third of the thread pitch h. A preferred value is $r_G = h/2$. The thread pitch h is 1.3 to 1.8 mm, preferably 1.5 mm.

The concave design of the thread turns can but need not be circular, and may be, for example, oval or designed in some other way. In this case, the greatest depth of the individual thread turns is preferably smaller than one-third of the thread pitch.

A thread designed with these parameters provides secure anchoring of the implant body in the jawbone and is at the same time designed to be adapted to the elasticity properties of the bone tissue, so that no voids are formed between the bone tissue and implant body.

The implant shoulder 4 formed at the upper end of the implant body 1 facilitates and improves straightening of the implant post after insertion of the implant.

Preferably, the ratio of the diameter $D_B$ to the length $L_B$ of the bending zone 6 is in the range of 1:1.5 to 1:3. A ratio of 1:2.6 is especially advantageous. The diameter in the bending zone generally lies in the range of 1.5 to 2 mm, preferably 1.7 mm. Surprisingly, it has been found that, at these lengths and ratios, a relatively large bending angle (i.e., up to 30°) can be achieved, whereby the size of the bending zone can be kept small, which is of special importance due to the tightness of the space conditions in the jaw region. The large bending angle that can be achieved has the advantage that the bore, which is screwed into the implant, does not have to be straightened in a prescribed manner with respect to the tooth replacement to be inserted. Regarding the straightening of the bore axis, the requirements are not as strict as in prior screw implants. This means that the bores can be made more continuously than the bores for prior screw implants.

Since the screw implant is screwed-in until the bending zone lies in the region of the gums, it is advantageous that the bending radius $r_b$ in the bending zone is smaller than or equal to 3 mm when the bending angle $\alpha_B$ is equal to 30°. This small bending radius permits that the bending at the gum region is limited.

In order to make it possible to correct an already straightened implant post, it is important that the number of bendings of the bending zone, when the implant post is bent back and forth at a bending angle of 30 degrees, is approximately 3 to 4. This means that it is possible to straighten the implant head several times without the implant neck developing cracks or without the implant post breaking off completely. This permits much more exact work than with the screw implants of the prior art.

In spite of the high flexibility offered by the screw implant according to the invention, the tensile strength of the implant neck can still be at least 2400 N at a bending angle of 30 degrees.

According to a preferred embodiment, the implant neck has at least one widening transition section which borders on the bending zone and has a radius of curvature $r_A$ of 2 to 3 mm. This transition region can be arranged either between the bending zone and the screw thread or between the bending zone and the implant post. Since, as described above, the implant neck with the bending zone lies in the region of the gum, it is especially important that, after straightening the implant post, the gum lies tightly at the implant neck without the development of voids. A radius of curvature of 2 to 3 mm in these transition regions permits one to prevent the development of voids, due to the elasticity properties of the gums.

Due to the shape of the implant body, automatic centering occurs during the insertion process according to a predetermined bore channel. The diameter of the implant is kept small.

In order to insert the implant, a preliminary bore is made with a small implant drill, the diameter of which is smaller than the largest diameter of the implant body. This is a small intervention in which the bone tissue is not cut and only very little bone tissue is removed. The implant is then introduced axially through the prebored implant bed.

In order to facilitate insertion of the implant body, the two opposed flat areas 8 at the upper end of the implant post 7 accept a rectangular key of a straightening device.

With the aid of a probe, the depth of the alveolar chamber to the countercorticalis can be accurately measured and established through the bore channel and thus the length of the implant body can be determined. In case the implant to be inserted is somewhat longer than the base channel, the implant can be shortened by grinding the implant foot to the required length. Care must be taken that the implant foot is spherical so that it can be supported on the countercorticalis without damage to the bone tissue. The radius of the spherical tip 2a is preferably 0.5 mm.

The final insertion of the screw implant can be done in simple, continuous working steps, namely by preboring a narrow channel, or implant bed, measuring the required length of the implant body and, if necessary, shortening this body at the implant foot, screwing-in of the implant and straightening of the implant post. With the screw implant according to the invention, one can always achieve optimum accuracy of adaptation and implant position. During the bending process, adjustment parallel to the other teeth or vertical to the ridge of the jaw can be checked and compared.

The foregoing detailed description is given for clearness of understanding only, and no unnecessary limitations should be understood therefrom, as modifications within the scope of the invention will be apparent to those skilled in the art.

I claim:

1. A screw implant for a jawbone comprising:
   a threaded conical implant body adapted to be screwed into a jawbone; and
   an attachment defining an implant neck and a conical implant post to accept a replacement tooth or substructure;
   said implant body comprising a compression thread comprising concave thread turns; and
   said compression thread defining an outer boundary cone having an angle of opening $\alpha_1$ and a core having a core angle $\alpha_2$, the ratio $\alpha_1:\alpha_2$ being in the range of 1:0.6 to 1:1.

2. The screw implant of claim 1 wherein said greatest depth of said individual thread turns is about one-third of the pitch h of said thread.

3. The screw implant of claim 1 wherein said thread turns have the shape of a circular arc and a radius of curvature $r_G$ of each thread turn greater than or equal to one-third of the pitch h of said thread.

4. The screw implant of claim 3 wherein said radius of curvature $r_G$ is equal to h/2.

5. The screw implant of claim 1 wherein an implant shoulder is formed at the upper end of said implant body, said shoulder extending into said implant neck and defining a bending zone, said implant post being formed on a conical broadening region of said implant neck.

6. The screw implant of claim 5 wherein said bending zone has a diameter $D_B$ and a length $L_B$, the ratio $D_B:L_B$ being in the range of 1:1.5 to 1:3.

7. The screw implant of claim 5 wherein said implant neck has at least one broadening transition region bordering the bending zone and having a radius of curvature $r_A$ of 2 to 3 mm.

8. The screw implant of claim 5 wherein said bending zone has a bending radius $r_B$ of less than or equal to 3 mm at a bending zone angle $\alpha_B$ of 30 degrees.

9. The screw implant of claim 5 wherein the number of bendings of said bending zone is 3 to 4 when the implant post is bent back and forth by 30 degrees.

10. The screw implant of claim 5 wherein the tensile strength of said implant neck is at least 2400 N at a bending angle $\alpha_B$ of 30 degrees.

11. The screw implant of claim 1 wherein two flat areas opposite to one another are defined in an upper end region of said implant post in order to accept a rectangular key of a straightening tool.

12. The screw implant of claim 1 wherein a free end of said implant post defines as a spherical head.

13. The screw implant of claim 1 comprising a titanium alloy having a surface passivated with a protective layer of titanium oxide.

* * * * *